United States Patent [19]

Edwards et al.

[11] Patent Number: 6,010,679
[45] Date of Patent: *Jan. 4, 2000

[54] TERNARY RADIOPHARMACEUTICAL COMPLEXES

[76] Inventors: David Scott Edwards, 123 Farms Dr., Burlington, Mass. 01803; Shuang Liu, 17 Judith Rd., Chelmsford, Mass. 01824

[*] Notice: This patent is subject to a terminal disclaimer.

[21] Appl. No.: 09/013,320

[22] Filed: Jan. 26, 1998

Related U.S. Application Data

[63] Continuation of application No. 08/415,908, Apr. 3, 1995, Pat. No. 5,744,120, which is a continuation-in-part of application No. 08/218,861, Mar. 28, 1994, Pat. No. 5,879,657, which is a continuation-in-part of application No. 08/040,336, Mar. 30, 1993, abandoned.

[51] Int. Cl.$^7$ ............................ A61K 51/00; A61M 36/14
[52] U.S. Cl. ........................ 424/1.69; 424/1.65; 534/10; 534/14; 530/17; 514/9; 514/11
[58] Field of Search .................... 424/1.11, 1.49, 424/1.53, 1.65, 1.69, 9.1, 1.37; 534/7, 10–16; 530/300, 317; 514/9, 11

[56] References Cited

U.S. PATENT DOCUMENTS 5,066,789  11/1991  Srinivasan et al. ...................... 530/388
5,300,278  4/1994  Pasqualini et al. ........................ 534/14
5,350,837  9/1994  Bridger et al. ............................ 534/14
5,744,120  4/1998  Edwards et al. ........................ 424/1.69

FOREIGN PATENT DOCUMENTS 8908657  9/1989  WIPO .

*Primary Examiner*—Jose' G. Dees
*Assistant Examiner*—Dameron Jones

[57] ABSTRACT

This invention provides novel radiopharmaceuticals which are useful as imaging agents for the diagnosis of cardiovascular disorders, infectious disease and cancer. The radiopharmaceuticals are comprised of phosphine or arsine ligated technetium-99m labeled hydrazino or diazino modified biologically active molecules that selectively localize at sites of disease and thus allow an image to be obtained of the loci using gamma scintigraphy. This invention also provides methods for using the radiopharmaceuticals and kits comprising radiopharmaceutical precursors. The radiopharmaceuticals of this invention have the structure:

$$[(Q)_d{'}L_n-C_h{'}]_{k}-M_t(A_{L1})_y(A_{L2})z;$$

wherein the variables are as defined herein.

15 Claims, No Drawings

6,010,679

TERNARY RADIOPHARMACEUTICAL COMPLEXES

CROSS-REFERENCE TO RELATED APPLICATIONS

The present application is a continuation of application Ser. No. 08/415,908 filed on Apr. 3, 1995, now U.S. Pat. No. 5,744,120, which is a continuation-in-part of our application U.S. Ser. No. 08/218,861, filed Mar. 28, 1994, now U.S. Pat. No. 5,879,657 which is a continuation-in-part of U.S. Ser. No. 08/040,336 filed Mar. 30, 1993, now abandoned the disclosures of which are incorporated herein by reference.

FIELD OF THE INVENTION

This invention relates to novel radiopharmaceuticals which are useful as imaging agents for the diagnosis of cardiovascular disorders, infectious disease and cancer, and to kits useful for their preparation. The radiopharmaceuticals are comprised of phosphine or arsine ligated technetium-99m labeled hydrazino or diazino modified biologically active molecules that selectively localize at sites of disease and thus allow an image to be obtained of the loci using gamma scintigraphy.

BACKGROUND OF THE INVENTION

There is a current need for new methods for the non-invasive diagnosis of a variety of diseases such as thromboembolic disease, atherosclerosis, infection and cancer. Radiopharmaceuticals comprised of gamma-ray emitting radionuclide labeled biologically active molecules can fulfill the need. The biologically active molecules serve to localize the radionuclides at the sites of disease and thus allow the sites to be visualized by gamma scintigraphy. The molecules can be either proteins, antibodies, antibody fragments, peptides or polypeptides, or peptidomimetics. The molecules interact with a receptor or binding site expressed at the sites of the disease or with a receptor or binding site on an endogenous blood component, such as platelets and leukocytes, that accumulate at the sites. This interaction results in selective localization of a percentage of the injected radiopharmaceutical while the remainder is cleared either through the renal or hepatobiliary systems. The localized radiopharmaceutical is then imaged externally using gamma scintigraphy. The relative rates of sequestration, clearance and radionuclidic decay determine the ease of visualization, often expressed as the target-to-background ratio. Frequently, only certain portions of the biologically active molecules bind to the receptors; these portions are termed the recognition sequences or units.

A number of radiopharmaceuticals comprised of radionuclide labeled proteins, antibodies or antibody fragments are under development, however, to date only one has been approved by the Food and Drug Administration. This sparse record results from a combination of factors that make developing these radiopharmaceuticals difficult, including problems with manufacturing and quality control, non-optimal sequestration and clearance rates, and the occurence of antigenic or allergic responses to the radiopharmaceuticals. These problems are mainly due to the macromolecular nature of the proteins, antibodies and antibody fragments. Their high molecular weight makes direct chemical synthesis impractical, therefore they must be synthesized by recombinant or cloning techniques that typically give low yields and require extensive isolation and purification procedures. Their molecular weight can slow their rates of localization and preclude their clearance by an active elimination mechanism via the kidneys or liver, resulting in prolonged retention in the circulation which causes a high background level during imaging. Also, the body's immune system tends to recognize more efficiently larger exogenous species.

The use of lower molecular weight peptides, polypeptides or peptidomimetics as the biologically active molecules obviates a number of these problems. These molecules can be synthesized directly using classical solution chemistry or by an automated peptide synthesizer. They can be formed in higher yields and require less complicated purification procedures. They tend to clear more rapidly from the circulation by an active elimination pathway resulting in a lower background in the images. They are also usually not immunogenic. The first radionuclide labeled polypeptide radiopharmaceutical has been recently approved by the Food and Drug Administration.

There are two general methods for labeling biologically active molecules with radionuclides for use as radiopharmaceuticals termed direct and indirect labeling. Direct labeling involves attaching the radionuclide to atoms on the biologically active molecule; while the indirect method involves attaching the radionuclide via a chelator. The chelator can either be attached to the biologically active molecule prior to reaction with the radionuclide or the radionuclide labeled chelator moiety can be attached to the biologically active molecule. Several recent reviews describe these labeling methods and are incorporated herein by reference: S. Jurisson et. al., Chem. Rev., 1993, 93, 1137; A. Verbruggen, Eur. J. Nuc. Med., 1990, 17, 346; and M. Derwanjee, Semin. Nuc. Med., 1990, 20, 5.

The use of hydrazines and hydrazides as chelators to modify proteins for labeling with radionuclides has been recently disclosed in Schwartz et. al., U.S. Pat. No. 5,206,370. For labeling with technetium-99m, the hydrazino-modified protein is reacted with a reduced technetium species, formed by reacting pertechnetate with a reducing agent in the presence of a chelating dioxygen ligand. The technetium becomes bound to the protein through what are believed to be hydrazido or diazenido linkages with the coordination sphere completed by the ancillary dioxygen ligands. Examples of ancillary dioxygen ligands include glucoheptonate, gluconate, 2-hydroxyisobutyrate, and lactate.

Certain dioxygen ligands have been recently reported to be particularly advantageous for labeling hydrazino-modified proteins with technetium-99m. Bridger et. al., European Patent Application 93302712.0, disclose a series of functionalized aminocarboxylates the use of which are reported to improve the labeling process of hydrazino-modified macromolecules such as monoclonal antibodies. The improvements are manifest by shorter reaction times and higher specific activities. Examples of these improved dioxygen ligands include hydroxyalkyl substituted glycine derivatives such as tricine.

In co-pending U.S. Ser. No. 08/218,861 (equivalent to WO 94/22494), filed Mar. 28, 1993, the synthesis of novel radiolabeled platelet IIb/IIIa receptor antagonists as imaging agents for thromboembolic disorders is disclosed. These reagents comprise radionuclide labeled chelator modified cyclic compounds. A preferred chelator for modifying the cyclic compounds is the hydrazino or diazenido moiety.

The present invention provides novel technetium-99m labeled hydrazino or diazino modified biologically active molecules that are formed as a minimal number of isomers, the relative ratios of which do not change with time. These compounds are more straightforward to develop, requiring less complicated manufacturing and labeling process controls.

SUMMARY OF THE INVENTION

This invention provides novel radiopharmaceuticals which are useful as imaging agents for the diagnosis of cardiovascular disorders, such as thromboembolic disease or atherosclerosis, infectious disease and cancer. The radiopharmaceuticals are comprised of phosphine or arsine ligated technetium-99m labeled hydrazino or diazenido modified biologically active molecules that selectively localize at sites of disease and thus allow an image to be obtained of the loci using gamma scintigraphy. The invention also provides methods of using said radiopharmaceuticals as imaging agents for the diagnosis of cardiovascular disorders, such as thromboembolic disease or atherosclerosis, infectious disease and cancer. It further provides kits for the preparation of said radiopharmaceuticals.

DETAILED DESCRIPTION OF THE INVENTION

The present invention is directed to novel radiopharmaceuticals for the diagnosis of cardiovascular disorders, such as thromboembolic disease and atherosclerosis, infectious disease or cancer of the formula, methods of using said radiopharmaceuticals in the diagnosis of diseases and kits useful for the preparation of said radiopharmaceutical.

[1] One embodiment of the present prevention is a radiopharmaceutical comprising a transition metal radionuclide, a transition metal chelator, a biologically active group connected to said chelator, a first ancillary ligand, a second ancillary ligand capable of stabilizing the radiopharmaceutical, optionally having a linking group between said chelator and said biologically active group.

[2] Another embodiment of the present invention is a radiopharmaceutical of embodiment [1] having a linking group between said chelator and said biologically active group.

[3] Another embodiment of the present invention is a radiopharmaceutical of embodiment [2] of formula:

$$[(Q)_{d'}L_n-C_h']_x-M_t(A_{L1})_y(A_{L2})_z \quad (1)$$

wherein:
Q is a biologically active molecule;
d' is 1 to 20;
$L_n$ is a linking group of formula:

wherein:
$M^1$ is $—[(CH_2)_gZ^1]_{g'}—(CR^{55}R^{56})_{g''}—$;
$M^2$ is $—(CR^{55}R^{56})_{g''}—[Z^1(CH_2)_g]_{g'}—$;
g is independently 0–10;
g' is independently 0–1;
g" is independently 0–10;
f is independently 0–10;
f' is independently 0–10;
f" is independently 0–1;
$Y^1$ and $Y^2$, at each occurrence, are independently selected from:
a bond, O, $NR^{56}$, C=O, C(=O)O, OC(=O)O, C(=O)NH—, C=$NR^{56}$, S, SO, $SO_2$, $SO_3$, NHC(=O), $(NH)_2C$(=O), $(NH)_2C$=S;
$Z^1$ is independently selected at each occurrence from a $C_6–C_{14}$ saturated, partially saturated, or aromatic carbocyclic ring system, substituted with 0–4 $R^{57}$; and a heterocyclic ring system, optionally substituted with 0–4 $R^{57}$;
$R^{55}$ and $R^{56}$ are independently selected at each occurrence from:
hydrogen; $C_1–C_{10}$ alkyl substituted with 0–5 $R^{57}$; alkaryl wherein the aryl is substituted with 0–5 $R^{57}$;
$R^{57}$ is independently selected at each occurrence from the group: hydrogen, OH, $NHR^{58}$, C(=O) $R^{58}$, OC(=O)$R^{58}$, OC(=O)$OR^{58}$, C(=O)$OR^{58}$, C(=O) $NR^{58}$—, C=N, $SR^{58}$, $SOR^{58}$, $SO_2R^{58}$, $NHC(=O)R^{58}$, $NHC(=O)NHR^{58}$, NHC(=S) $NHR^{58}$; or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C$(=O), $(NH)_2C$=S; and,
$R^{58}$ is independently selected at each occurrence from the group: hydrogen; $C_1–C_6$ alkyl; benzyl, and phenyl;
x and y are independently 1 or 2;
z is independently 1–4;
$M_t$ is a transition metal radionuclide selected from the group: $^{99m}$Tc, $^{186}$Re and $^{188}$Re;
$C_h'$ is a radionuclide metal chelator coordinated to transition metal radionuclide $M_t$, and is independently selected at each occurrence, from the group: $R^{40}$N=N$^+$=, $R^{40}R^{41}$N-N=, $R^{40}$N=, and $R^{40}$N=N (H)—, wherein
$R^{40}$ is independently selected at each occurrence from the group: a bond to $L_n$, $C_1–C_{10}$ alkyl substituted with 0–3 $R^{52}$, aryl substituted with 0–3 $R^{52}$, cycloaklyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;
$R^{41}$ is independently selected from the group: hydrogen, aryl substituted with 0–3 $R^{52}$, $C_1–C_{10}$ alkyl substituted with 0–3 $R^{52}$, and a heterocycle substituted with 0–3 $R^{52}$;
$R^{52}$ is independently selected at each occurrence from the group: a bond to $L_n$, =O, F, Cl, Br, I, —$CF_3$, —CN, —$CO_2R^{53}$, —C(=O)$R^{53}$, —C(=O)N$(R^{53})_2$, —CHO, —$CH_2OR^{53}$, —OC(=O)$R^{53}$, —OC(=O) $OR^{53a}$, —$OR^{53}$, —OC(=O)N$(R^{53})_2$, —$NR^{53}$C (=O)$R^{53}$, —$NR^{54}$C(=O)$OR^{53a}$, —$NR^{53}$C(=O)N $(R^{53})_2$, —$NR^{54}SO_2N(R^{53})_2$, —$NR^{54}SO_2NR^{53a}$, —$SO_3H$, —$SO_2R^{53a}$, —$SR^{53}$, —S(=O)$R^{53a}$, —$SO_2N(R^{53})_2$, —N$(R^{53})_2$, —NHC(=NH)$NHR^{53}$, —C(=NH)$NHR^{53}$, =$NOR^{53}$, $NO_2$, —C(=O) $NHOR^{53}$, —C(=O)$NHNR^{53}R^{53a}$, —$OCH_2CO_2H$, 2-(1-morpholino)ethoxy;
$R^{53}$, $R^{53a}$, and $R^{54}$ are each independently selected at each occurrence from the group: hydrogen, $C_{1-C6}$ alkyl, and a bond to $L_n$;
$A_{L1}$ is a first ancillary ligand selected from the group: dioxygen ligand,
functionalized aminocarboxylate, and
halide;
$A_{L2}$ is an ancillary ligand capable of stabilizing the radiopharmaceutical selected from the group:
$A^9$ and $A^{10}$—W—$A^{11}$,
wherein:
$A^9$ is independently selected at each occurrence from the group: $PR^{61}R^{62}R^{63}$ and $AsR^{61}R^{62}R^{63}$;

$A^{10}$ and $A^{11}$ are independently selected at each occurrence from the group: $PR^{61}R^{62}$ and $AsR^{61}R^{62}$;

W is a spacer group selected from the group: $C_1$–$C_{10}$ alkyl substituted with 0–3 $R^{70}$, aryl substituted with 0–3 $R^{70}$, cycloaklyl substituted with 0–3 $R^{70}$, heterocycle substituted with 0–3 $R^{70}$, heterocycloalkyl substituted with 0–3 $R^{70}$, aralkyl substituted with 0–3 $R^{70}$ and alkaryl substituted with 0–3 $R^{70}$;

$R^{61}$, $R^{62}$, and $R^{63}$ are independently selected at each occurrence from the group: $C_1$–$C_{10}$ alkyl substituted with 0–3 $R^{70}$, aryl substituted with 0–3 $R^{70}$, cycloalkyl substituted with 0–3 $R^{70}$, heterocycle substituted with 0–3 $R^{70}$, aralkyl substituted with 0–3 $R^{70}$, alkaryl substituted with 0–3 $R^{70}$, and arylalkaryl substituted with 0–3 $R^{70}$;

$R^{70}$ is independently selected at each occurrence from the group: F, Cl, Br, I, —CF3, —CN, —$CO_2R^{71}$, —C(=O)$R^{71}$, —C(=O)N($R^{71}$)$_2$, —$CH_2OR^{71}$, —OC(=O)$R^{71}$, —OC(=O)$OR^{71a}$, —$OR^{71}$, —OC(=O)N($R^{71}$)$_2$, —$NR^{71}$C(=O)$R^{71}$, —$NR^{71}$C(=O)$OR^{71}$, —$NR^{71}$C(=O)N($R^{71}$)$_2$, $SO_3^-$, —$NR^{71}SO_2$N($R^{71}$)$_2$, —$NR^{71}SO_2R^{71a}$, —$SO_3H$, —$SO_2R^{71}$, —S(=O)$R^{71}$, —$SO_2$N($R^{71}$)$_2$, —N($R^{71}$)$_2$, —N($R^{71}$)$_3^+$, —NHC(=NH)$NHR^{71}$, —C(=NH)$NHR^{71}$, =$NOR^{71}$, $NO_2$, —C(=O)$NHOR^{71}$, —C(=O)$NHNR^{71}R^{71a}$, —$OCH_2CO_2H$; and $R^{71}$ and $R^{71a}$ are independently selected at each occurrence from the group: hydrogen and $C_1$–$C_6$ alkyl; and pharmaceutically acceptable salts thereof.

[4] Another embodiment of the present invention is a radiopharmaceutical of embodiment [3] wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

$L_n$ is:

wherein:

g" is 0–5;

f is 0–5;

f' is 1–5;

$Y^1$ and $Y^2$, at each occurrence, are independently selected from:
O, $NR^{56}$, C=O, C(=O)O, OC(=O)O, C(=O)NH—, C=$NR^{56}$, S, SO, $SO_2$, $SO_3$, NHC(=O), (NH)$_2$C(=O), (NH)$_2$C=S;

$R^{55}$ and $R^{56}$ are independently selected at each occurrence from: hydrogen, $C_1$–$C_{10}$ alkyl, and alkaryl;

x and y are independently 1 or 2;

z is independently 1–2;

$M_t$ is $^{99m}$Tc;

$C_{h'}$ is a radionuclide metal chelator coordinated to transition metal radionuclide $M_t$, and is independently selected at each occurrence, from the group: $R^{40}$N=N$^+$=, $R^{40}R^{41}$N—N=, $R^{40}$N=, and $R^{40}$N=N(H)—;

$R^{40}$ is independently selected at each occurrence from the group: aryl substituted with 0–3 $R^{52}$, and heterocycle substituted with 0–3 $R^{52}$;

$R^{41}$ is independently selected from the group: hydrogen, aryl substituted with 0–1 $R^{52}$, $C_1$–$C_3$ alkyl substituted with 0–1 $R^{52}$, and a heterocycle substituted with 0–1 $R^{52}$;

$R^{52}$ is independently selected at each occurrence from the group: a bond to $L_n$, —$CO_2R^{53}$, —$CH_2OR^{53}$, —$SO_3H$, —$SO_2R^{53a}$, —N($R^{53}$)$_2$, —N($R^{53}$)$_3^+$, —NHC(=NH)$NHR^{53}$, and —$OCH_2CO_2H$;

$R^{53}$, $R^{53a}$ are each independently selected at each occurrence from the group: hydrogen and $C_1$–$C_3$ alkyl;

$A_{L1}$ is selected from the group:
pyrones, pyridinones, and functionalized aminocarboxylates;

$A_{L2}$ is selected from the group:
$A^9$ and $A^{10}$—W—$A^{11}$,
wherein:
$A^9$ is $PR^{61}R^{62}R^{63}$;
$A^{10}$ and $A^{11}$ are $PR^{61}R^{62}$;

W is a spacer group selected from the group: $C_1$–$C_3$ alkyl substituted with 0–3 $R^{70}$, aryl substituted with 0–3 $R^{70}$, and heterocycle substituted with 0–3 $R^{70}$;

$R^{61}$, $R^{62}$, and $R^{63}$ are independently selected at each occurrence from the group: $C_1$–$C_3$ alkyl substituted with 0–3 $R^{70}$, aryl substituted with 0–3 $R^{70}$, and heterocycle substituted with 0–3 $R^{70}$;

$R^{70}$ is independently selected at each occurrence from the group: —$CO_2R^{71}$, —$OR^{71}$, —$SO_3$— and —$SO_3H$; and $R^{71}$ is hydrogen.

[5] Another embodiment of the present invention is a radiopharmaceutical of embodiment [4] wherein:

Q represents a biologically active molecule selected from the group: IIb/IIIa receptor antagonists and chemotactic peptides;

d' is 1;

$L_n$ is:

wherein:

g" is 0–5;

f is 0–5;

f' is 1–5;

$Y^1$ and $Y^2$, at each occurrence, are independently selected from:
O, $NR^{56}$, C=O, C(=O)O, OC(=O)O, C(=O)NH—, C=$NR^{56}$, S, NHC(=O), (NH)$_2$C(=O), (NH)$_2$C=S;

$R^{55}$ and $R^{56}$ are hydrogen;

x and y are 1;

z is 1;

$C_{h'}$ is a radionuclide metal chelator coordinated to transition metal radionuclide Mt, and is independently selected at each occurrence, from the group: $R^{40}$N=N$^+$=, and $R^{40}R^{41}$N-N=;

$R^{40}$ is independently selected at each occurrence from the group: heterocycle substituted with $R^{52}$;

$R^{41}$ is hydrogen;

$R^{52}$ is a bond to $L_n$;

$A_{L1}$ is tricine;

$A_{L2}$ is $PR^{61}R^{62}R^{63}$, wherein
$R^{61}$, $R^{62}$, and $R^{63}$ are independently selected at each occurrence from the group: $C_1$–$C_3$ alkyl substituted with 0–3 $R^{70}$, aryl substituted with 0–3 $R^{70}$;

$R^{70}$ is independently selected at each occurrence from the group: $—CO_2H$, $—OH$, $—SO_3H$, $—SO_3^-$.

[5] Another embodiment of the present invention is the radiopharmaceutical of embodiment [3] wherein:

Q is

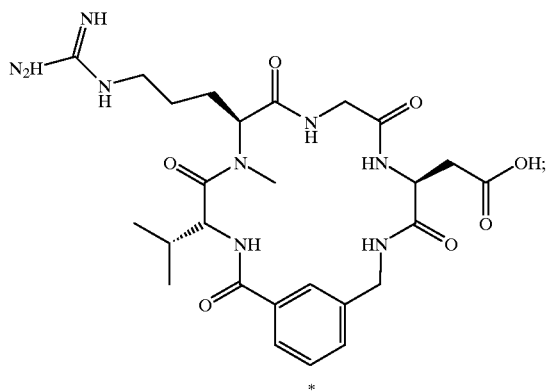

d' is 1;

$L_n$ is attached to Q at the carbon atom designated with a * and has the formula:

$—(C=O)NH(CH_2)_5C=(O)NH—$;

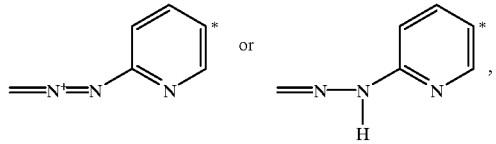

$C_{h'}$ is
and is attached to $L_n$ at the carbon atom designated with a *;

$M_t$ is $^{99m}Tc$;

$A_{L1}$ is tricine;

$A_{L2}$ is $PR^{61}R^{62}R^{63}$, wherein $R^{61}$, $R^{62}$ and $R^{63}$ are each phenyl bearing an $SO_3H$ or $SO_3^-$ group in the meta position; and x, y and z are 1.

[7] Another embodiment of the present invention is the radiopharmaceutical of embodiment [3] wherein:

Q is

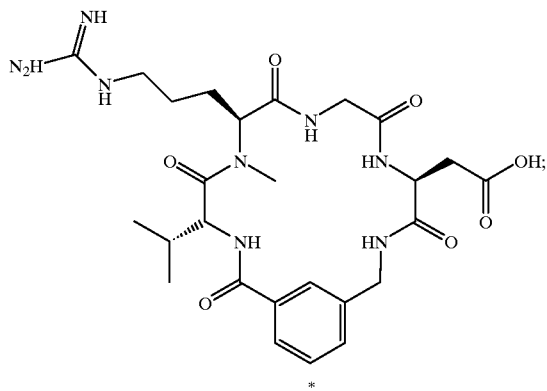

d' is 1;

$L_n$ is attached to Q at the carbon atom designated with a * and has the formula:

$—(C=O)NH(CH_2)_5C=(O)NH—$;

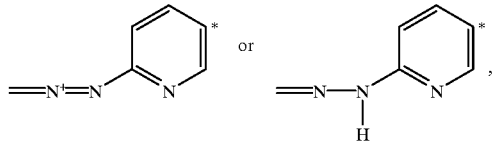

$C_{h'}$ is
and is attached to $L_n$ at the carbon atom designated with a *;

$M_t$ is $^{99m}Tc$;

$A_{L1}$ is tricine;

$A_{L2}$ is $PR^{61}R^{62}R^{63}$, wherein $R^{61}$ is phenyl, $R^{62}$ and $R^{63}$ are each phenyl bearing an $SO_3H$ or $SO_3^-$ group in the meta position; and x, y and z are 1.

[8] Another embodiment of the present invention is the radiopharmaceutical of embodiment [3] wherein:

Q is

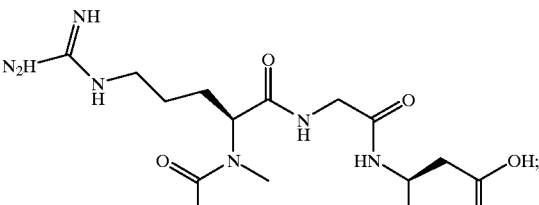

d' is 1;

$L_n$ is attached to Q at the carbon atom designated with a * and has the formula:

$—(C=O)NH(CH_2)_5C(=O)NH—$;

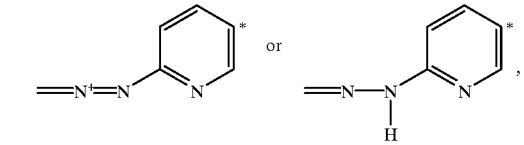

$C_{h'}$ is
and is attached to $L_n$ at the carbon atom designated with a *;

$M_t$ is $^{99m}Tc$;

$A_{L1}$ is tricine;

$A_{L2}$ is $PR^{61}R^{62}R^{63}$, wherein $R^{61}$ and $R^{62}$ are phenyl, and $R^{63}$ is phenyl bearing an $SO_3H$ or $SO_3^-$ group in the meta position; and x, y and z are 1.

[9] Another embodiment of the present invention is the radiopharmaceutical of embodiment [3] wherein:

Q is

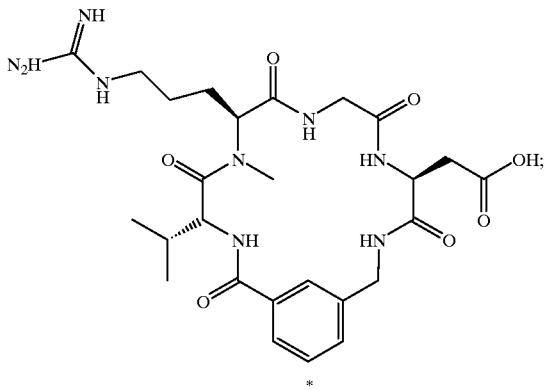

d' is 1;

$L_n$ is attached to Q at the carbon atom designated with a * and has the formula:

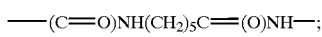

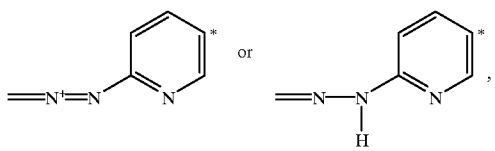

$C_{h'}$ is
    and is attached to $L_n$ at the carbon atom designated with a *;

$M_t$ is $^{99m}Tc$;

$A_{L1}$ is tricine;

$A_{L2}$ is $PR^{61}R^{62}R^{63}$, wherein $R^{61}$, $R^{62}$ and $R^{63}$ are each p-(2-phenylethyl)phenyl wherein the phenylethyl bears an $SO_3H$ or $SO_3^-$ group in the para position; and x, y and z are 1.

embodiment [10] Another embodiment of the present invention is the radiopharmaceutical of embodiment [3] wherein:

Q is

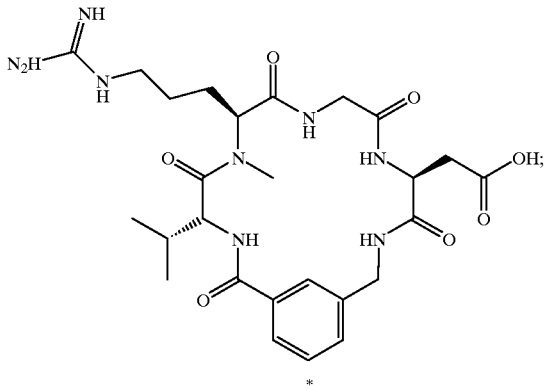

d' is 1;

$L_n$ is attached to Q at the carbon atom designated with a * and has the formula:

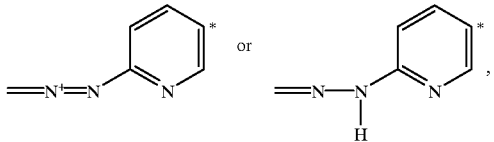

$C_{h'}$ is and is attached to $L_n$ at the carbon atom designated with a *;

$M_t$ is $^{99m}Tc$;

$A_{L1}$ is tricine;

$A_{L2}$ is $PR^{61}R^{62}R^{63}$, wherein $R^{61}$, $R^{62}$ and $R^{63}$ are each p-(2-phenylpropyl)phenyl wherein the phenylpropyl bears an $SO_3H$ or $SO_3^-$ group in the para position; and x, y and z are 1.

[11] Another embodiment of the present invention is the radiopharmaceutical of embodiment [3] wherein:

Q is

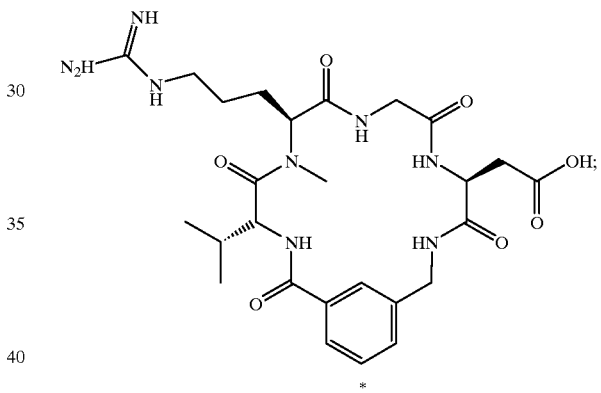

d' is 1;

$L_n$ is attached to Q at the carbon atom designated with a * and has the formula:

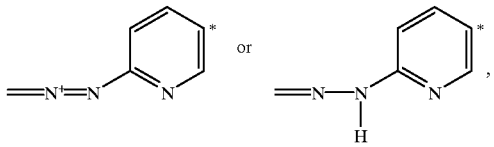

$C_{h'}$ is
    and is attached to $L_n$ at the carbon atom designated with a *;

$M_t$ is $^{99m}Tc$;

$A_{L1}$ is tricine;

$A_{L2}$ is $R^{61}R^{62}PCH_2CH_2PR^{61}R^{62}$, wherein $R^{61}$, $R^{62}$ are each phenyl substituted with an $SO_3H$ or $SO_3^-$ group in the meta position; and x, y and z are 1.

[12] Another embodiment of the present invention is the radiopharmaceutical of embodiment [3] wherein:

Q is

[structure: cyclic peptide containing arginine-like guanidino group, Gly, Asp(OH), Val, N-methyl amide, and meta-substituted benzyl group, with * designation]

d' is 1;

$L_n$ is attached to Q at the carbon atom designated with a * and has the formula:

—(C=O)NH(CH$_2$)$_5$C(=O)NH—;

[structures: —N⁺=N—(2-pyridyl)* or —N=N—NH—(2-pyridyl)*], $C_{h'}$ is
and is attached to $L_n$ at the carbon atom designated with a *;

$M_t$ is $^{99m}$Tc;

$A_{L1}$ is tricine;

$A_{L2}$ is PR$^{61}$R$^{62}$R$^{63}$, wherein R$^{61}$, R$^{62}$ and R$^{63}$ are C$_3$-alkyl substituted with 1 OH group; and x, y and z are 1.

[13] Another embodiment of the present invention is the radiopharmaceutical of embodiment [3] wherein:

Q is

[structure: cyclic peptide analogous to above]

d' is 1;

$L_n$ is attached to Q at the carbon atom designated with a * and has the formula:

—(C=O)NH(CH$_2$)$_5$C(=O)NH—;

[structures: —N⁺=N—(2-pyridyl)* or —N=N—NH—(2-pyridyl)*], $C_{h'}$ is
and is attached to $L_n$ at the carbon atom designated with a *;

$M_t$ is $^{99m}$Tc;

$A_{L1}$ is tricine;

$A_{L2}$ is PR$^{61}$R$^{62}$R$^{63}$, wherein R$^{61}$, R$^{62}$ and R$^{63}$ are CH$_2$CH$_2$COOH; and x, y and z are 1.

[14] Another embodiment of the present invention is the radiopharmaceutical of embodiment [3] wherein:

Q is

[structure: cyclic peptide analogous to above]

d' is 1;

$L_n$ is attached to Q at the carbon atom designated with a * and has the formula:

—(C=O)NH(CH$_2$)$_5$C(=O)NH—;

[structures: —N⁺=N—(2-pyridyl)* or —N=N—NH—(2-pyridyl)*], $C_{h'}$ is
and is attached to $L_n$ at the carbon atom designated with a *;

$M_t$ is $^{99m}$Tc;

$A_{L1}$ is kojic acid;

$A_{L2}$ is PR$^{61}$R$^{62}$R$^{63}$, wherein R$^{61}$, R$^{62}$ and R$^{63}$ are each phenyl bearing an SO$_3$H or SO$_3^-$ group in the meta position;

x and z are 1; and y is 2.

[15] Another embodiment of the present invention is a method for radioimaging a mammal comprising (i) administering to said mammal an effective amount of a radiopharmaceutical of any of embodiments [1]-[14], and (ii) scanning the mammal using a radioimaging device.

[16] Another embodiment of the present invention is a method for visualizing sites of platelet deposition in a mammal by radioimaging, comprising (i) administering to said mammal an effective amount of a radiopharmaceutical of any of embodiments [6]–[14], and (ii) scanning the mammal using a radioimaging device.

[17] Another embodiment of the present invention is a method of determining platelet deposition in a mammal comprising administering to said mammal a radiopharmaceutical composition of any of embodiments [6]–[14], and imaging said mammal.

[18] Another embodiment of the present invention is a method of diagnosing a disorder associated with platelet deposition in a mammal comprising administering to said mammal a radiopharmaceutical composition of any of embodiments [6]–[14], and imaging said mammal.

[19] Another embodiment of the present invention is a kit for preparing a radiopharmaceutical comprising:

(a) a predetermined quantity of a sterile, pharmaceutically acceptable reagent of formulae:

$(Q)_{d'}L_n-C_h;$ (b) a predetermined quantity of a sterile, pharmaceutically acceptable first ancillary ligand, $A_{L1}$, selected from the group:
dioxygen ligand,
functionalized aminocarboxylate, and
halide; and (c) a predetermined quantity of a sterile, pharmaceutically acceptable second ancillary ligand, $A_{L2}$, selected from the group:
$A^9$ and $A^{10}—W—A^{11};$ wherein:
Q is a biologically active molecule;
d' is 1 to 20;
$L_n$ is a linking group of formula:

$M^1-[Y^1(CR^{55}R^{56})_f(Z^1)_{f'}Y^2]_{f''}-M^2,$ wherein:
$M^1$ is $—[(CH_2)_gZ^1]_{g'}—(CR^{55}R^{56})_{g''}—;$
$M^2$ is $—(CR^{55}R^{56})_{g''}—[Z^1(CH_2)_g]_{g'}—;$
g is independently 0–10;
g' is independently 0–1;
g" is independently 0–10;
f is independently 0–10;
f' is independently 0–10;
f" is independently 0–1;
$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, $(NH)_2C=S;$
$Z^1$ is independently selected at each occurrence from a $C_6–C_{14}$ saturated, partially saturated, or aromatic carbocyclic ring system, substituted with 0–4 $R^{57};$ and a heterocyclic ring system, optionally substituted with 0–4 $R^{57};$
$R^{55}$ and $R^{56}$ are independently selected at each occurrence from: hydrogen; $C_1–C_{10}$ alkyl substituted with 0–5 $R^{57};$ alkaryl wherein the aryl is substituted with 0–5 $R^{57};$
$R^{57}$ is independently selected at each occurrence from the group: hydrogen, OH, $NHR^{58}$, $C(=O)R^{58}$, $OC(=O)R^{58}$, $OC(=O)OR^{58}$, $C(=O)OR^{58}$, C(=O)$NR^{58}$—, C=N, $SR^{58}$, $SOR^{58}$, $SO_2R^{58}$, NHC(=O)$R^{58}$, NHC(=O)$NHR^{58}$, NHC(=S)$NHR^{58};$ or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C(=O)$, $(NH)_2C=S;$ and, $R^{58}$ is independently selected at each occurrence from the group: hydrogen; $C_1–C_6$ alkyl; benzyl, and phenyl;

$C_h$ is a radionuclide metal chelator independently selected at each occurrence from the group: $R^{40}R^{41}N—N=C(C_1–C_3\ alkyl)_2$ and $R^{40}NNH_2—,$ wherein::

$R^{40}$ is independently selected at each occurrence from the group: a bond to $L_n$, $C_1–C_{10}$ alkyl substituted with 0–3 $R^{52}$, aryl substituted with 0–3 $R^{52}$, cycloakly substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52};$ $R^{41}$ is independently selected from the group: hydrogen, aryl substituted with 0–3 $R^{52}$, $C_1–C_{10}$ alkyl substituted with 0–3 $R^{52}$, and a heterocycle substituted with 0–3 $R^{52};$ $R^{52}$ is independently selected at each occurrence from the group: a bond to $L_n$, =O, F, Cl, Br, I, —$CF_3$, —CN, —$CO_2R_{53}$, —C(=O)$R^{53}$, —C(=O)N$(R^{53})_2$, —CHO, —$CH_2OR^{53}$, —OC(=O)$R^{53}$, —OC(=O)$OR^{53a}$, —$OR^{53}$, —OC(=O)N$(R^{53})_2$, —$NR^{53}$C(=O)$R^{53}$, —$NR^{54}$C(=O)$OR^{53a}$, —$NR^{53}$C(=O)N$(R^{53})_2$, —$NR^{54}SO_2N(R^{53})_2$, —$NR^{54}SO_2R^{53a}$, —$SO_3H$, —$SO_2R^{53a}$, —$SR^{53}$, —S(=O)$R^{53a}$, —$SO_2N(R^{53})_2$, —N$(R^{53})_2$, —NHC(=NH)$NHR^{53}$, —C(=NH)$NHR^{53}$, =$NOR^{53}$, $NO_2$, —C(=O)$NHOR^{53}$, —C(=O)$NHNR^{53}R^{53a}$, —$OCH_2CO_2H$, 2-(1-morpholino)ethoxy;

$R^{53}R^{53a}$, and $R^{54}$ are each independently selected at each occurrence from the group: hydrogen, $C_1–C_6$ alkyl, and a bond to $L_n;$ $A^9$ is independently selected at each occurrence from the group: $PR^{61}R^{62}R^{63}$ and $AsR^{61}R^{62}R^{63};$ $A^{10}$ and $A^{11}$ are independently selected at each occurrence from the group: $PR^{61}R^{62}$ and $AsR^{61}R^{62};$ W is a spacer group selected from the group: $C_1–C_{10}$ alkyl substituted with 0–3 $R^{70}$, aryl substituted with 0–3 $R^{70}$, cycloaklyl substituted with 0–3 $R^{70}$, heterocycle substituted with 0–3 $R^{70}$, heterocycloalkyl substituted with 0–3 $R^{70}$, aralkyl substituted with 0–3 $R^{70}$ and alkaryl substituted with 0–3 $R^{70};$ $R^{61}$, $R^{62}$, and $R^{63}$ are independently selected at each occurrence from the group: $C_1–C_{10}$ alkyl substituted with 0–3 $R^{70}$, aryl substituted with 0–3 $R^{70}$, cycloalkyl substituted with 0–3 $R^{70}$, heterocycle substituted with 0–3 $R^{70}$, aralkyl substituted with 0–3 $R^{70}$, alkaryl substituted with 0–3 $R^{70}$, and arylalkaryl substituted with 0–3 $R^{70};$ $R^{70}$ is independently selected at each occurrence from the group: F, Cl, Br, I, —$CF_3$, —CN, —$CO_2R^{71}$, —C(=O)$R^{71}$, —C(=O)N$(R^{71})_2$, —$CH_2OR^{71}$, —OC(=O)$R^{71}$, —OC(=O)$OR^{71a}$, —$OR^{71}$, —OC(=O)N$(R^{71})_2$, —$NR^{71}$C(=O)$R^{71}$, —$NR^{71}$C(=O)$OR^{71}$, —$NR^{71}$C(=O)N$(R^{71})_2$, $SO_3$—, —$NR^{71}SO_2N(R^{71})_2$, —$NR^{71}SO_2R^{71a}$, —$SO_3H$, —$SO_2R^{71}$, —S(=O)$R^{71}$, —$SO_2N(R^{71})_2$, —N$(R^{71})_2$, —N$(R^{71})_3$+, —NHC(=NH)$NHR^{71}$, —C(=NH)$NHR^{71}$, =$NOR^{71}$, $NO_2$, —C(=O)$NHOR^{71}$, —C(=O)$NHNR^{71}R^{71a}$, —$OCH_2CO_2H$; and $R^{71}$ and $R^{71a}$ are independently selected at each occurrence from the group: hydrogen and $C_1–C_6$ alkyl.

[20] Another embodiment of the present invention is the kit of embodiment [19] wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

$L_n$ is:

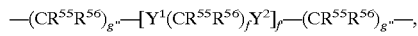

wherein:
g" is 0–5;
f is 0–5;
f' is 1–5;
$Y^1$ and $Y^2$, at each occurrence, are independently selected from:
O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, $(NH)_2C=S$;
$R^{55}$ and $R^{56}$ are independently selected at each occurrence from: hydrogen, C1–$C_{10}$ alkyl, and ($C_1$–$C_{10}$ alkyl)aryl;
$A_{L1}$ is selected from the group:
pyrones, pyridinones, and functionalized aminocarboxylates;
$A_{L2}$ is selected from the group:
$A^9$ and $A^{10}$—W—$A^{11}$,
wherein:
$A^9$ is $PR^{61}R^{62}R^{63}$;
$A^{10}$ and $A^{11}$ are $PR^{61}R^{62}$;
W is a spacer group selected from the group: $C_1$–$C_3$ alkyl substituted with 0–3 $R^{70}$, aryl substituted with 0–3 $R^{70}$, and heterocycle substituted with 0–3 $R^{70}$;
$R^{61}$, $R^{62}$, and $R^{63}$ are independently selected at each occurrence from the group: $C_1$–$C_3$ alkyl substituted with 0–3 $R^{70}$, aryl substituted with 0–3 $R^{70}$, and heterocycle substituted with 0–3 $R^{70}$;
$R^{70}$ is independently selected at each occurrence from the group: —$CO_2R^{71}$, —$OR^{71}$, —$SO_3^-$ and —$SO_3H$; and
$R^{71}$ is hydrogen.

[21] Another embodiment of the present invention is the kit of embodiment [20] wherein:

Q is a biologically active molecule selected from the group: IIb/IIIa receptor antagonists, and chemotactic peptides;
d' is 1;
$L_n$ is:

wherein:
g" is 0–5;
f is 0–5;
f' is 1–5;
$Y^1$ and $Y^2$, at each occurrence, are independently selected from:
O, $NR^{56}$, C=O, C(=O)O, OC(=O)O, C(=O)NH—, C=$NR^{56}$, S, NHC(=O), $(NH)_2C(=O)$, $(NH)_2C=S$;
$R^{55}$ and $R^{56}$ are hydrogen;
$A_{L1}$ is tricine;
$A_{L2}$ is $PR^{61}R^{62}R^{63}$, wherein
$R^{61}$, $R^{62}$, and $R^{63}$ are independently selected at each occurrence from the group: $C_1$–$C_3$ alkyl substituted with 0–3 $R^{70}$, aryl substituted with 0–3 $R^{70}$; and
$R^{70}$ is independently selected at each occurrence from the group: —$CO_2H$, —OH, —$SO_3H$, —$SO_3^-$.

[22] Another embodiment of the present invention is the kit of embodiment [21] wherein:

Q is

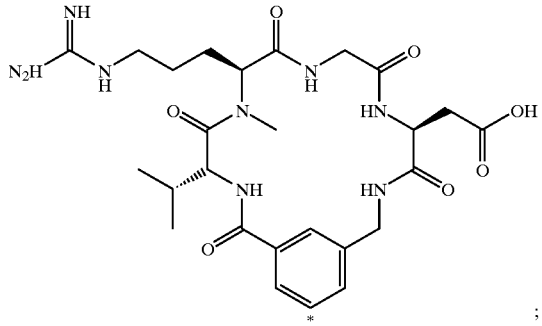

d' is 1;
$L_n$ is attached to Q at the carbon atom designated with a * and has the formula:

—(C=O)NH$(CH_2)_5$C(=O)NH—;

$A_{L2}$ is $PR^{61}R^{62}R^{63}$, wherein $R^{61}$, $R^{62}$ and $R^{63}$ are each phenyl bearing an $SO_3H$ or $SO_3^-$ group in the meta position.

[23] Another embodiment of the present invention is the kit of embodiment [21] wherein:

Q is

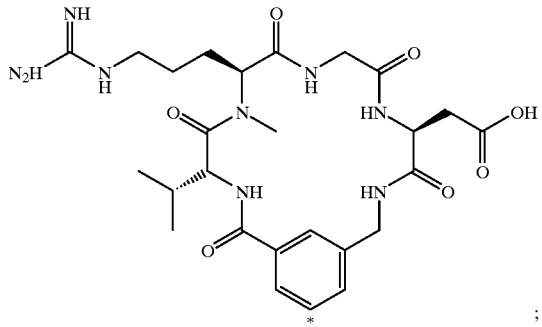

d' is 1;
$L_n$ is attached to Q at the carbon atom designated with a * and has the formula:

—(C=O)NH$(CH_2)_5$C(=O)NH—;

$A_{L2}$ is $PR^{61}R^{62}R^{63}$, wherein $R^{61}$ is phenyl, $R^{62}$ and $R^{63}$ are each phenyl bearing an $SO_3H$ or $SO_3^-$ group in the meta position.

[24] Another embodiment of the present invention is the kit of embodiment [21] wherein:

Q is

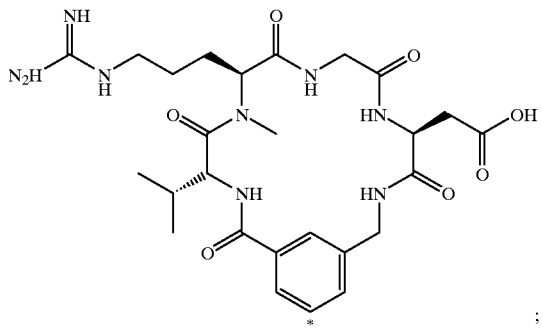

d' is 1;

$L_n$ is attached to Q at the carbon atom designated with a * and has the formula:

—(C=O)NH(CH$_2$)$_5$C(=O)NH—;

$A_{L2}$ is PR$^{61}$R$^{62}$R$^{63}$, wherein R$^{61}$ and R$^{62}$ are phenyl, and R$^{63}$ is phenyl bearing an SO$_3$H or SO$_3^-$ group in the meta position.

[25] Another embodiment of the present invention is the kit of embodiment [21] wherein:

Q is

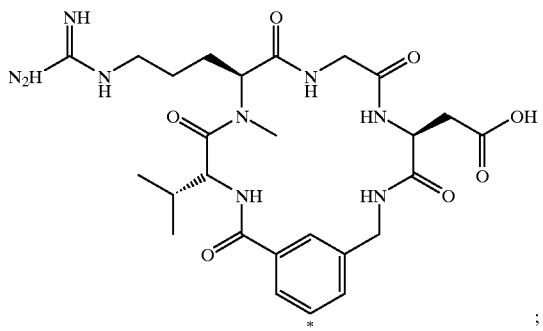

d' is 1;

$L_n$ is attached to Q at the carbon atom designated with a * and has the formula:

—(C=O)NH(CH$_2$)$_5$C(=O)NH—;

$A_{L2}$ is PR$^{61}$R$^{62}$R$^{63}$, wherein R$^{61}$, R$^{62}$ and R$^{63}$ are each p-(2-phenylethyl)phenyl wherein the phenylethyl bears an SO$_3$H or SO$_3^-$ group in the para position.

[26] Another embodiment of the present invention is the kit of embodiment [21] wherein:

Q is

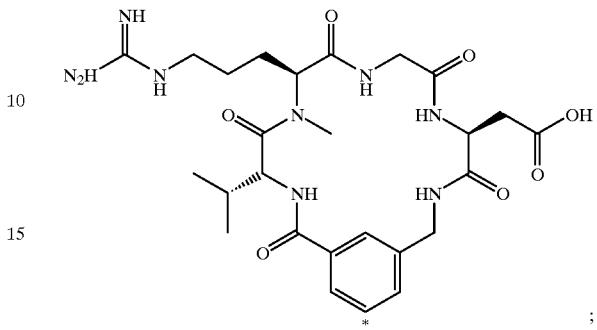

d' is 1;

$L_n$ is attached to Q at the carbon atom designated with a * and has the formula:

—(C=O)NH(CH$_2$)$_5$C(=O)NH—;

$A_{L2}$ is PR$^{61}$R$^{62}$R$^{63}$, wherein R$^{61}$, R$^{62}$ and R$^{63}$ are each p-(2-phenylpropyl)phenyl wherein the phenylpropyl bears an SO$_3$H or SO$_3^-$ group in the para position.

[27] Another embodiment of the present invention is the kit of embodiment [21] wherein:

Q is

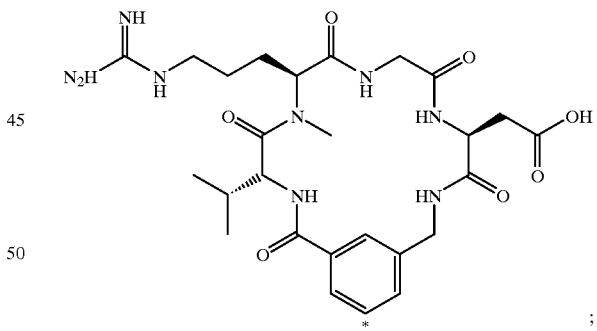

d' is 1;

$L_n$ is attached to Q at the carbon atom designated with a * and has the formula:

—(C=O)NH(CH$_2$)$_5$C(=O)NH—;

$A_{L2}$ is R$^{61}$R$^{62}$PCH$_2$CH$_2$PR$^{61}$R$^{62}$, wherein R$^{61}$, R$^{62}$ are each phenyl substituted with an SO$_3$H or SO$_3^-$ group in the meta position.

[28] Another embodiment of the present invention is the kit of embodiment [21] wherein:

Q is

[cyclic peptide structure containing Arg, Val, N-Me, Gly, Asp, and meta-substituted benzyl group, with * marking attachment carbon]

d' is 1;

$L_n$ is attached to Q at the carbon atom designated with a * and has the formula:

—(C=O)NH(CH$_2$)$_5$C(=O)NH—;

$A_{L2}$ is PR$^{61}$R$^{62}$R$^{63}$, wherein R$^{61}$, R$^{62}$ and R$^{63}$ are C$_3$-alkyl substituted with 1 OH group.

[29] Another embodiment of the present invention is the kit of embodiment [21] wherein:

Q is

[cyclic peptide structure containing Arg, Val, N-Me, Gly, Asp, and meta-substituted benzyl group, with * marking attachment carbon]

d' is 1;

$L_n$ is attached to Q at the carbon atom designated with a * and has the formula:

—(C=O)NH(CH$_2$)$_5$C(=O)NH—;

$A_{L2}$ is PR$^{61}$R$^{62}$R$^{63}$, wherein R$^{61}$, R$^{62}$ and R$^{63}$ are CH$_2$CH$_2$COOH.

[30] Another embodiment of the present invention is the kit of embodiment [20] wherein:

Q is

[cyclic peptide structure containing Arg, Val, N-Me, Gly, Asp, and meta-substituted benzyl group, with * marking attachment carbon]

d' is 1;

$L_n$ is attached to Q at the carbon atom designated with a * and has the formula:

—(C=O)NH(CH$_2$)$_5$C(=O)NH—;

$A_{L1}$ is kojic acid;

$A_{L2}$ is PR$^{61}$R$^{62}$R$^{63}$, wherein R$^{61}$, R$^{62}$ and R$^{63}$ are each phenyl bearing an SO$_3$H or SO$_3^-$ group in the meta position.

[31] Another embodiment of the invention is the kits of any of embodiments [19]–[30] wherein a reducing agent is also present.

[32] A preferred embodiment of the invention is the kits of embodiment [31] wherein the reducing agent is stannous chloride.

When any variable occurs more than one time in any constituent or in any formula, its definition on each occurrence is independent of its definition at every other occurrence. Thus, for example, if a group is shown to be substituted with 0–2 R$^{52}$, then said group may optionally be substituted with up to two R$^{52}$ and R$^{52}$ at each occurrence is selected independently from the defined list of possible R$^{52}$. Also, by way of example, for the group —N(R$^{53}$)$_2$, each of the two R$^{53}$ substituents on N is independently selected from the defined list of possible R$^{53}$. Combinations of substituents and/or variables are permissible only if such combinations result in stable compounds.

By "stable compound" or "stable structure" is meant herein a compound that is sufficiently robust to survive isolation to a useful degree of purity from a reaction mixture, and formulation into an efficacious diagnostic agent.

The term "capable of stabilizing", as used herein to describe the second ancillary ligand $A_{L2}$, means that the ligand is capable of coordinating to the transition metal radionuclide in the presence of the first ancillary ligand and the transition metal chelator, under the conditions specified herein, resulting in a radiopharmaceutical of Formula 1 having a minimal number of isomeric forms, the relative ratios of which do not change significantly with time, and that remains substantially intact upon dilution.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the *CRC Handbook of Chemistry and Physics*, 65th Edition, CRC Press, Boca Raton, Fla., 1984, as any substance which yields ions, other than hydrogen or hydroxyl ions.

As used herein, "alkyl" is intended to include both branched and straight-chain saturated aliphatic hydrocarbon groups having the specified number of carbon atoms; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl and adamantyl; and "bicycloalkyl" is intended to include saturated bicyclic ring groups such as [3.3.0]bicyclooctane, [4.3.0]bicyclononane, [4.4.0] bicyclodecane (decalin), [2.2.2]bicyclooctane, and so forth.

As used herein, "aryl" or "aromatic residue" is intended to mean phenyl or naphthyl, which when substituted, the substitution can be at any position.

As used herein, the term "heterocycle" or "heterocyclic ring system" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H,6H-1,5, 2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, 9-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl", means an aryl group bearing an alkyl group of 1–10 carbon atoms bearing an aryl group; and the term "heterocycloalkyl" means an alkyl group of 1–10 carbon atoms bearing a heterocycle.

The biologically active molecule Q can be a protein, antibody, antibody fragment, peptide or polypeptide, or peptidomimetic that is comprised of a recognition sequence or unit for a receptor or binding site expressed at the site of the disease, or for a receptor or binding site expressed on platelets or leukocytes. The exact chemical composition of Q is selected based on the disease state to be diagnosed, the mechanism of localization to be utilized, and to provide an optimium combination of rates of localization, clearance and radionuclidic decay.

For the purposes of this invention, the term thromboembolic disease is taken to include both venous and arterial disorders and pulmonary embolism, resulting from the formation of blood clots.

For the diagnosis of thromboembolic disorders or atherosclerosis, Q is selected from the group including the cyclic IIb/IIIa receptor antagonist compounds described in co-pending U.S. Ser. No. 08/218,861 (equivalent to WO 94/22494); the RGD containing peptides described in U.S. Pat. Nos. 4,578,079, 4,792,525, the applications PCT US88/04403, PCT US89/01742, PCT US90/03788, PCT US91/02356 and by Ojima et. al., 204th Meeting of the Amer. Chem. Soc., 1992, Abstract 44; the peptides that are fibrinogen receptor antagonists described in European Patent Applications 90202015.5, 90202030.4, 90202032.2, 90202032.0, 90311148.2, 90311151.6, 90311537.6, the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB 9313965.7; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem., 1992, 35, 4640; or oxidized low density lipoprotein (LDL).

For the diagnosis of infection, inflammation or transplant rejection, Q is selected from the group including the leukocyte binding peptides described in PCT W093/17719 (excluding the technetium binding group), PCT W092/13572 (excluding the technetium binding group) or U.S. Ser. No. 08-140000; the chemotactic peptides described in Eur. Pat. Appl. 90108734.6 or A. Fischman et. al., Semin. Nuc. Med., 1994, 24, 154; or the leukostimulatory agents described in U.S. Pat. No. 5,277,892.

For the diagnosis of cancer, Q is selected from the group of somatostatin analogs described in UK Application 8927255.3 or PCT W094/00489, the selectin binding peptides described in PCT W094/05269, the biological-function domains described in PCT W093/12819, Platelet Factor 4 or the growth factors (PDGF, EGF, FGF, TNF MCSF or Il1-8).

Q may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of nitrogen and oxygen donor atoms. Examples include but are not limited to: iminodiacetic acid, 2,3 diaminopropionic acid, nitrilotriacetic acid, N,N'-ethylenediamine diacetic acid, N,N,N'-ethylenediamine triacetic acid, hydroxyethylethylenediamine triacetic acid, N,N'-ethylenediamine bis-hydroxyphenylglycine, or the ligands described in Eur. Pat. Appl. 93302712.0. (The names for the ligands in these examples refer to either the protonated or non-protonated forms of the ligands.)

The radiopharmaceuticals of the present invention for the diagnosis of thromboembolic disease can be easily prepared by admixing a salt of a radionuclide, a reagent of Formula 2, an ancillary ligand $A_{L1}$, an ancillary ligand $A_{L2}$, and optionally a reducing agent, in an aqueous solution at temperatures from room temperature to 100° C.

(2)

and pharmaceutically acceptable salts thereof, wherein: Q, d', $L_n$ are as defined above and $C_h$ is a radionuclide metal chelator independently selected at each occurrence from the group: $R^{40}R^{41}N-N=C(C_1-C_3 \text{ alkyl})_2$ and $R^{40}NNH_2-$, wherein $R^{40}$, $R^{41}$ are as described above, and pharmaceutically acceptable salts thereof.

Alternatively, the radiopharmaceuticals of the present invention can be prepared by first admixing a salt of a radionuclide, an ancillary ligand $A_{L1}$, and a reducing agent in an aqueous solution at temperatures from room temperature to 100° C. to form an intermediate radionuclide complex with the ancillary ligand $A_{L1}$ then adding a reagent of Formula 2 and an ancillary ligand $A_{L2}$ and reacting further at temperatures from room temperature to 100° C.

Alternatively, the radiopharmaceuticals of the present invention can be prepared by first admixing a salt of a radionuclide, an ancillary ligand $A_{L1}$, a reagent of Formula 2, and a reducing agent in an aqueous solution at temperatures from room temperature to 100° C. to form an intermediate radionuclide complex, as described in co-pending U.S. Ser. No. 08/218,861 (equivalent to WO 94/22494), and then adding an ancillary ligand $A_{L2}$ and reacting further at temperatures from room temperature to 100° C.

The total time of preparation will vary depending on the identity of the radionuclide, the identities and amounts of the reactants and the procedure used for the preparation. The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

The radionuclides for the present invention are selected from the group $^{99m}$Tc, $^{186}$Re, or $^{188}$Re. For diagnostic purposes $^{99m}$Tc is the preferred isotope. Its 6 hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy, however, they also emit high energy beta particles that are more damaging to living tissues. These beta particle emissions can be utilized for therapeutic purposes, for example, cancer radiotherapy.

The salt of $^{99m}$Tc is preferably in the chemical form of pertechnetate and a pharmaceutically aceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The reagents of Formula 2 can be synthesized as described in co-pending U.S. Ser. No. 08/218,861 (equivalent to WO 94/22494). The amount of the reagents used to prepare the radiopharmaceuticals of the present invention can range from 0.1 μg to 10 mg, or more preferably from 0.5 μg to 100 μg. The amount used will be dictated by the amounts of the other reactants and the identity of the radiopharmaceuticals of Formula 1 to be prepared.

The ancillary ligands $A_{L1}$ used to synthesize the radiopharmaceuticals of the present invention can either be synthesized or obtained from commercial sources and include, halides, dioxygen ligands and functionalized aminocarboxylates. Dioxygen ligands are ligands that coordinate to the radionuclide through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2- or 3,4-hydroxypyridinones, or pharmaceutically acceptable salts thereof.

Functionalized aminocarboxylates include ligands that coordinate to the radionuclide through a combination of nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, N,N'-ethylenediamine bis-hydroxyphenylglycine, or the ligands described in Eur. Pat. Appl. 93302712.0, or pharmaceutically acceptable salts thereof.

Halides can be fluoride, chloride, bromide or iodide.

The selection of an ancillary ligand $A_{L1}$ is determined by several factors including the chemical and physical properties of the ancillary ligand, the rate of formation, the yield, and the number of isomeric forms of the resulting radiopharmaceuticals, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

A series of functionalized aminocarboxylates are disclosed by Bridger et. al. that result in improved rates of formation of technetium labeled hydrazino modified proteins. we have determined that certain of these aminocarboxylates result in improved yields and a minimal number of isomeric forms of the radiopharmaceuticals of the present invention. The preferred ancillary ligands $A_{L1}$ are the dioxygen ligands pyrones or pyridinones and functionalized aminocarboxylates that are derivatives of glycine; the most preferred is tricine (tris(hydroxymethyl)methylglycine).

The amounts of the ancillary ligands $A_{L1}$ used can range from 0.1 mg to 1 g, or more preferrably from 1 mg to 100 mg. The exact amount for a particular radiopharmaceutical is a function of the the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of ALI will result in other by-products such as reduced hydrolyzed technetium, or technetium colloid.

The preferred ancillary ligands $A_{L2}$ are trisubstituted phosphines or trisubstituted arsines. The substituents can be alkyl, aryl, alkoxy, heterocycle, aralkyl, alkaryl and arylalkaryl and may or may not bear functional groups comprised of heteroatoms such as oxygen, nitrogen, phosphorus or sulfur. Examples of such functional groups include but are not limited to: hydroxyl, carboxyl, carboxamide, ether, ketone, amino, ammonium, sulfonate, sulfonamide, phosphonate, and phosphonamide. These phosphine and arsine ligands can be obtained either from commercial sources or can be synthesized by a variety of methods known to those skilled in the art. A number of methods can be found in Kosolapoff and Maier, *Organic Phosphorus Compounds*: Wiley-Interscience: New York, 1972; Vol. 1.

The selection of an ancillary ligand $A_{L2}$ is determined by several factors including the chemical and physical properties of the ancillary ligand, the rate of formation, the yield, and the number of isomeric forms of the resulting radiopharmaceuticals, and the suitability of the ligand for a lyophilized kit formulation. Preferred ancillary ligands for the present invention are those that bear at least one functionality. The presence of the functionality effects the chemical and physical properties of the ancillary ligands such as basicity, charge, lipophilicity, size, stability to oxidation, solubility in water, and physical state at room temperature. The preferred ancillary ligands have a solubility in water of at least 0.001 mg/mL. This solubility allows the ligands to be used to synthesize the radiopharmaceuticals of the present invention without an added solublizing agent or co-solvent.

The more preferred ancillary ligands $A_{L2}$ include trisubstituted phosphines and trisubstituted arsines that have at least one functionality comprised of the heteroatoms oxygen, sulfur or nitrogen. These ligands can either be obtained commercially or synthesized. References for the synthesis of specific more preferred ligands can be obtained as follows: Tris(3-sulfonatophenyl)phosphine, sodium salt (TPPTS) was synthesized as described in Bartik et. al., Inorg. Chem., 1992, 31, 2667. Bis(3-sulfonatophenyl) phenylphosphine, sodium salt (TPPDS) and (3-sulfonatophenyl)diphenylphosphine, sodium salt (TPPMS) were synthesized as described in Kuntz, E., U.S. Pat. No. 4,248,802. Tris(2-(p-sulfonatophenyl)ethyl) phosphine, sodium salt (TPEPTS) and Tris(3-(p-sulfonatophenyl)propyl)phosphine, sodium salt (TPPPTS) were prepared as described in Bartik et. al., Organometallics, 1993, 12, 164. 1,2-Bis[bis(3-sulfonatophenyl)phosphino]ethane, sodium salt (DPPETS) was synthesized as described in Bartik et. al., Inorg. Chem., 1994, 33, 164. References for the

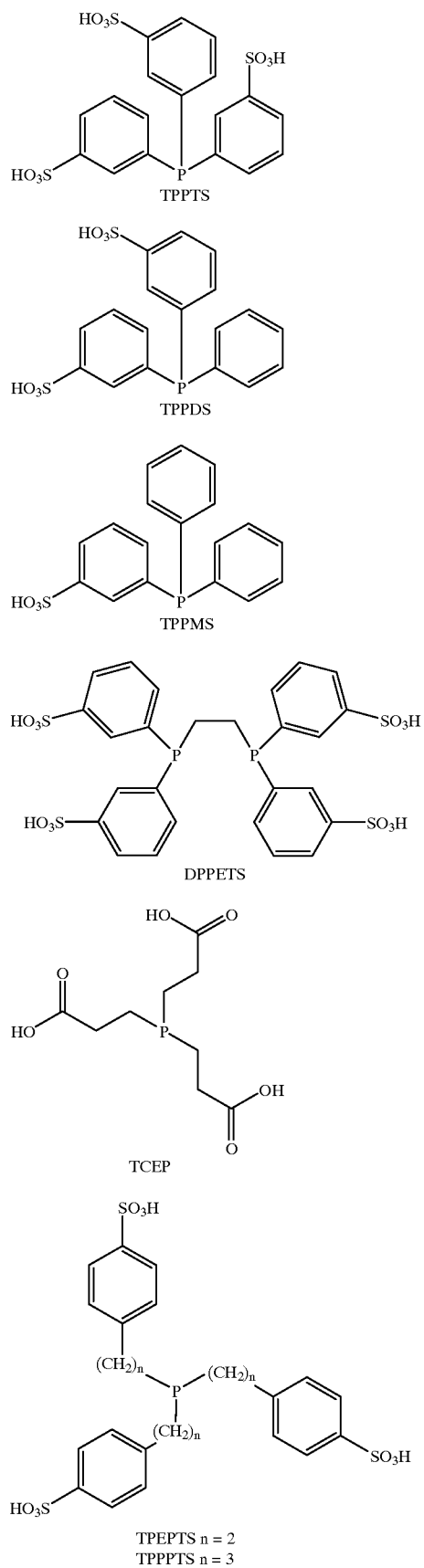

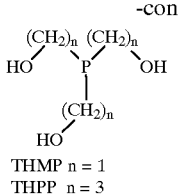

THMP n = 1
THPP n = 3 synthesis of other more preferred ancillary ligands $A_{L2}$ include Kuntz, E., Br. U.S. Pat. No. 1,540,242, Sinou, D., et. al., J. Chem. Soc. Chem Commun., 1986, 202, and Ahrland, S., et. al., J. Chem. Soc., 1950, 264, 276.

The more preferred ligands $A_{L2}$ have at least one functionality comprised of heteroatoms which do not bind to the technetium in competition with the donor atoms of the ancillary ligand $A_{L1}$ or the hydrazino or diazino moiety of the reagents of Formula 2. The ligands bind only through the phosphorus or arsenic donors. This insures that the resulting radiopharmaceuticals of Formula 1 are formed as a mixture of a minimal number of isomeric forms. The ligands are also hydrophilic as evidenced by a solubility in water of at least 0.01 mg/mL. This insures that a sufficient concentration can be used to synthesize the radiopharmaceuticals in high yield. There is no maximum solubility limit for use in this invention. Therefore, the hydrophilicity of the more preferred ancillary ligands $A_{L2}$ can still cover a wide range.

The charge and hydrophilicity of the ancillary ligand will effect the charge and hydrophilicity of the radiopharmaceuticals. As can be seen in Table 1, the hydrophilicity of a series of radiopharmaceuticals of Formula 1 that differ only in the identity of the ancillary ligand $A_{L2}$ varies systematically as determined by the retention times on reverse-phase HPLC.

The amounts of the ancillary ligands $A_{L2}$ used can range from 0.001 mg to 1 g, or more preferably from 0.01 mg to 10 mg. The exact amount for a particular radiopharmaceutical is a function of the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$.

A reducing agent can optionally be used for the synthesis of the radiopharmaceuticals of Formula 1. Suitable reducing agents include stannous salts, dithionite or bisulfite salts, borohydride salts, and formamidinesulfinic acid, wherein the salts are of any pharmaceutically acceptable form. The preferred reducing agent is a stannous salt. The use of a reducing agent is optional because the ancillary ligand $A_{L2}$ can also serve to reduce the Tc-99m-pertechnetate. The amount of a reducing agent used can range from 0.001 mg to 10 mg, or more preferably from 0.005 mg to 1 mg.

Kits in accord with the present invention comprise a sterile, non-pyrogenic, mixture of a reagent of Formula 2, an ancillary ligand $A_{L1}$, an ancillary ligand $A_{L2}$, and optionally a reducing agent. Preferably, such kits are comprised of a lyophilized mixture of a predetermined amount of a reagent of Formula 2, a predetermined amount of an ancillary ligand $A_{L1}$, a predetermined amount of an ancillary ligand $A_{L2}$, and optionally a predetermined amount of a reducing agent. The kits may also optionally include a bulking agent or lyophilization aid or a buffer. A list of acceptable bulking agents or lyophilization aids and a list of acceptable buffers can be found in the United States Pharmacopeia.

The specific structure of a radiopharmaceutical of the present invention will depend on the identity of the biologically active molecule Q, the number d', the identity of the linker $L_n$, the identity of the chelator moiety $C_{h'}$, the identity of the ancillary ligand $A_{L1}$, the identity of the ancillary ligand $A_{L2}$, and the identity of the radionuclide $M_r$. The identities of Q, $L_n$, and $C_h$, and the number d' are determined by the choice of the reagent of Formula 2. For a given reagent of Formula 2, the amount of the reagent, the amount and identity of the ancillary ligands $A_{L1}$ and $A_{L2}$, the identity of the radionuclide $M_r$ and the synthesis conditions employed will determine the structure of the radiopharmaceutical of Formula 1.

Radiopharmaceuticals synthesized using concentrations of reagents of Formula 2 of <100 µg/mL, will be comprised of one hydrazido or diazenido group $C_{h'}$; the value of x will be 1. Those synthesized using >1 mg/mL concentrations will be comprised of two hydrazido or diazenido groups; the value of x will be 2. The two $C_{h'}$ groups may be the same or different. For most applications, only a limited amount of the biologically active molecule can be injected and not result in undesired side-effects, such as chemical toxicity, interference with a biological process or an altered biodistibution of the radiopharmaceutical. Therefore, the radiopharmaceuticals with x equal to 2, which require higher concentrations of the reagents of Formula 2 comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y can be an integer from 0 to 3, while the values of z can be an integer from 1 to 4. In combination, the values of y and z will result in a technetium coordination sphere that is made up of at least five and no more than seven donor atoms, preferably six donor atoms. For monodentate phosphines or arsines of the formula $A^9$, z can be an integer from 1 to 4; for bidentate phosphines or arsines of the formula $A^{10}$–$A^{11}$, z can be either 1 or 2. The preferred combination for monodentate phosphines or arsines is y equal to 1 or 2 and z equal to 1. The preferred combination for bidentate phosphines or arsines is y equal to 0 or 1 and z equal to 1 or 2.

The radiopharmaceuticals are injected intravenously, usually in saline solution, at a dose of 1 to 100 mCi per 70 kg body weight, or preferably at a dose of 5 to 50 mCi. Imaging is performed using known procedures.

EXAMPLE SECTION

The materials used to synthesize the radiopharmaceuticals of the present invention -_ described in the following examples were obtained as follows. The reagents of Formula 2 were synthesized as described in co-pending U.S. Ser. No. 08/218,861 (equivalent to WO 94/22494). The ancillary ligands tricine and Kojic Acid were obtained from Research Organics Inc. and Aldrich Chemical Co., respectively. The phosphines were synthesized as described above, except for tris(hydroxypropyl)phosphine which was obtained from Cytec Canada Limited and tris(carboxyethyl)phosphine which was obtained from Aldrich Chemical Co. Deionized water was obtained from a Milli-Q Water System and was of >18 MΩ quality. Technetium-99m-pertechnetate ($^{99m}TcO_4^-$) was obtained from a DuPont Pharma $^{99}Mo/^{99m}Tc$ generator. Stannous chloride dihydrate was obtained from Aldrich Chemical Co. D-Phe(OMe) was obtained from Bachem Bioscience Inc.

The following abbreviations are used herein:
TPPTS Tris(3-sulfonatophenyl)phosphine, sodium salt
TPPDS Bis(3-sulfonatophenyl)phenylphosphine, sodium salt TPPMS (3-sulfonatophenyl)diphenylphosphine, sodium salt
TPEPTS Tris(2-(p-sulfonatophenyl)ethyl)phosphine, sodium salt
TPPPTS Tris(3—(p-sulfonatophenyl)propyl)phosphine, sodium salt
THPP Tris(3-hydroxypropyl)phosphine
TCEP Tris(2-carboxyethyl)phosphine
DPPETS 1,2-Bis(bis(3-sulfonatophenyl)phosphino] ethane, sodium salt Example 1

Synthesis of $^{99m}$Tc(tricine)(TPPTS)-Cyclo(D-Val-NMeArg-Gly-Asp-Mamb(hydrazino-nicotinyl-5-Aca))

To a clean 10 cc vial was added 40 mg tricine dissolved in 0.7 mL deionized $H_2O$, 5 μg Cyclo(D-Val-NMeArg-Gly-Asp-Mamb(hydrazino-nicotinyl-5-Aca)) dissolved in $H_2O$, 20 mCi $^{99m}TcO_4^-$ in saline, 1 mg TPPTS dissolved in $H_2O$, and 20 μg $SnCl_2.2H_2O$ dissolved in 0.1 N HCl. The total reaction volume was 1–1.5 mL.
The pH of the solution was adjusted to 4 with 1 N HCl. The solution was heated at 50° C. for 30 minutes and then was analyzed by HPLC Method 1 and ITLC Method 1. Analytical and yield data are shown in Table 1.

Example 2

Synthesis of $^{99m}$Tc(tricine)(TPPDS)-Cyclo(D-Val-NMeArg-Gly-Asp-Mamb(hydrazino-nicotinyl-5-Aca))

The synthesis was performed as described in Example 1 substituting TPPDS as the phosphine co-ligand and heating at 80° C. for 30 minutes. Analytical and yield data are shown in Table 1.

Example 3

Synthesis of $^{99m}$Tc(tricine)(TPPMS)-Cyclo(D-Val-NMeArg-Gly-Asp-Mamb(hydrazino-nicotinyl-5-Aca))

The synthesis was performed as described in Example 2 substituting TPPMS as the phosphine co-ligand. Analytical and yield data are shown in Table 1.

Example 4

Synthesis of $^{99m}$Tc(tricine)(TPEPTS)-Cyclo(D-Val-NMeArg-Gly-Asp-Mamb(hydrazino-nicotinyl-5-Aca))

To a 10 cc vial was added 40 mg Tricine in 0.5 mL $H_2O$, 5 μg XV-120 in 100 μl $H_2O$, 50 mCi $^{99m}TcO_4^-$ in 0.5 mL 0.9% saline, 1.0 mg of TPEPTS in 0.2 mL $H_2O$, and 20 μg of $SnCl_2.2H_2O$ dissolved in 0.1 N HCl. Total Volume 1.4 mL. The pH of the solution was adjusted to 7 using 1 N NaOH. The solution was heated at 80 ° C. for 30 minutes and then was analyzed by HPLC Method 1 and ITLC Method 1. Analytical and yield data are shown in Table 1.

Example 5

Synthesis of $^{99m}$Tc(tricine)(TPPPTS)-Cyclo(D-Val-NMeArg-Gly-Asp-Mamb(hydrazino-nicotinyl-5-Aca))

The synthesis was performed as described in Example 4 substituting TPPPTS as the phosphine co-ligand. Analytical and yield data are shown in Table 1.

Example 6

Synthesis of $^{99m}$Tc(tricine)(DPPETS)-Cyclo(D-Val-NMeArg-Gly-Asp-Mamb(hydrazino-nicotinyl-5-Aca))

To a clean 10 cc vial was added 40 mg tricine dissolved in 0.7 mL deionized $H_2O$, 5 μg Cyclo(D-Val-NMeArg-Gly-Asp-Mamb(hydrazino-nicotinyl-5-Aca)) dissolved in $H_2O$, 20 mCi $^{99m}TcO_4^-$ in saline, and 20 μg $SnCl_2.2H_2O$ dissolved in 0.1 N HCl. The total reaction volume was 1–1.5 mL. The solution was maintained at room temperature for 5 minutes and then 1 mg DPPETS dissolved in $H_2O$ was added. The pH of the solution was adjusted to 4 and then the solution was heated at 80° C. for 20 minutes. The resulting solution was analyzed by HPLC Method 1 and ITLC Method 1. Analytical and yield data are shown in Table 1.

Example 7

Synthesis of $^{99m}$Tc(tricine)(THPP)-Cyclo(D-Val-NMeArg-Gly-Asp-Mamb(hydrazino-nicotinyl-5-Aca))

The reagent is synthesized in two steps by first forming the reagent $^{99m}$Tc(tricine)-Cyclo(D-Val-NMeArg-Gly-Asp-Mamb(hydrazino-nicotinyl-5-Aca)) and then reacting it with THPP.
Step 1. Synthesis of $^{99m}$Tc(tricine)-Cyclo(D-Val-NMeArg-Gly-Asp-Mamb(hydrazino-nicotinyl-5-Aca))
To a 10 mL vial was added 0.3 mL of $^{99m}TcO_4^-$ (~100 mCi/mL) in saline, followed by 10 μg of Cyclo(D-Val-NMeArg-Gly-Asp-Mamb(hydrazino-nicotinyl-5-Aca)) dissolved in saline, 20 mg tricine dissolved in water at pH 7, and 20 μg of $SnCl_2.2H_2O$ dissolved in 1 N HCl. The reaction mixture was allowed to stand at room temperature for 15–20 min. and then analyzed by HPLC Method 1 and ITLC Method 1. The complex was formed in 90–95% yield.
Step 2. Reaction with THPP
To the reaction solution above was added 5 mg of THPP dissolved in saline. The mixture was heated at 50° C. for 15–20 min. The resulting solution was analyzed by HPLC Method 1 and ITLC Method 1. Analytical and yield data are shown in Table 1.

Example 8

Synthesis of $^{99m}$Tc(tricine)(TCEP)-Cyclo(D-Val-NMeArg-Gly-Asp-Mamb(hydrazino-nicotinyl-5-Aca))

The reagent is synthesized in two steps by first forming the reagent $^{99m}$Tc(tricine)-Cyclo(D-Val-NMeArg-Gly-Asp-Mamb(hydrazino-nicotinyl-5-Aca)) and then reacting it with TCEP.
Step 1. Synthesis of $^{99m}$Tc(tricine)-Cyclo(D-Val-NMeArg-Gly-Asp-Mamb(hydrazino-nicotinyl-5-Aca))
To a 10 mL vial was added 40 mg tricine dissolved in 0.5 mL $H_2O$, 5 μg of Cyclo(D-Val-NMeArg-Gly-Asp-Mamb (hydrazino-nicotinyl-5-Aca)) dissolved in 100 μL water, 0.5 mL of $^{99m}TcO_4^-$ (~100 mCi/mL) in saline, and 20 μg of $SnCl_2.2H_2O$ dissolved in 1 N HCl. The total reaction volume was 1–1.5 mL. The reaction mixture was allowed to stand at room temperature for 15–20 min. and then analyzed by HPLC Method 1 and ITLC Method 1. The complex was formed in 90–95% yield.
Step 2. Reaction with TCEP
To the reaction solution above was added 1.0 mg of TCEP dissolved in 0.2 mL water. The pH was adjusted to 4 using 1 N HCl. The mixture was heated at 50° C. for 15–20 min. The resulting solution was analyzed by HPLC Method 1 and ITLC Method 1. Analytical and yield data are shown in Table 1. (The product exists as two resolvable isomeric forms.)

Example 9

Synthesis of $^{99m}$Tc(Kojic Acid)(TPPTS)-Cyclo(D-Val-NMeArg-Gly-Asp-Mamb(hydrazino-nicotinyl-5-Aca))

The synthesis was performed as described in Example 1, substituting Kojic Acid (30 mg) for the tricine. Analytical and yield data are shown in Table 1.

Example 10

Synthesis of $^{99m}$Tc(tricine)(TPPTS)(Hydrazino-nicotinyl-D-Phe(OMe))

Step 1. Synthesis of 2-Hydrazino-nicotinyl-D-Phe(OMe)

The synthesis was performed as described in copending U.S. Ser. No., Example 3, substituting D-Phe(OMe) for the Cyclo(D-Val-NMeArg-Gly-Asp-Mamb(5-Aca).

Step 2. Synthesis of $^{99m}$Tc(tricine)(TPPTS)(Hydrazino-nicotinyl-D-Phe(OMe))

The synthesis was performed as described in Example 1, substituting 2-hydrazino-nicotinyl-D-Phe(OMe) for the Cyclo(D-Val-NMeArg-Gly-Asp-Mamb(hydrazino-nicotinyl-5-Aca). The product is characterized by retention times of 17.6 and 18.0 minutes (HPLC Method 1) and is formed in 85% yield.

Purification

As a general rule, compounds provided by the methods described herein are pure, as shown by the analytical techniques described directly below. However, if greater purity is desired, compounds provided herein may be further purified on HPLC, by collecting the compound as it elutes from the HPLC column using method 1, shown below. The volatiles are then evaporated and the residue redissolved in a 2% tricine in saline solution.

Analytical Methods

HPLC Method 1
Column: Vydac, $C_{18}$, 250 mm×4.6 mm, 300 Å pore size
Flow: 1.0 mL/min
Solvent A: 10 mm sodium monophosphate, pH=6.0
Solvent B: 100% acetonitrile

| Gradient: | | | |
|---|---|---|---|
| 0% B | 30% B | 75% B | 0% B |
| 0 min | 15 min | 25 min | 30 min |

Detection by NaI probe
HPLC Method 2
Column: Zorbax-Rx, $C_{18}$, 250 mm×4.6 mm
Flow: 1.0 mL/min
Solvent A: 95% 5 mm tetrabutylammonium ion, 30 mm phosphate, pH=3.7; 5% acetonitrile
Solvent B: 20% solvent A in acetonitrile

| Gradient: | | | | |
|---|---|---|---|---|
| 0% B | 10% B | 40% B | 60% B | 100% B |
| 0 min | 20 min | 30 min | 35 min | 40 min |

Detection by NaI probe
ITLC Method 1
Gelman ITLC-SG strips, 1 cm×7.5 cm, developed in 1:1 acetone:saline (0.9%).

TABLE 1

Analytical and Yield Data for $^{99m}$Tc Reagents

| | HPLC Retention time Method 1 (min) | % Yield |
|---|---|---|
| Example 1 | 10.4 | 95 |
| Example 2 | 12.8 | 93 |
| Example 3 | 15.9 | 93 |
| Example 4 | 10.0 | 70 |
| Example 5 | 12.6 | 83 |
| Example 6 | 9.6 | 88 |
| Example 7 | 12.3 | 92 |
| Example 8 | 8.7, 9.2 | 70 |
| Example 9 | 9.3 | 80 |

The values reported in Table 1 were obtained using HPLC Method 1. One retention time is shown for most of these examples. The two species that comprise these radiopharmaceuticals are usually not completely resolved by this HPLC method. Typically there is a shoulder on the main peak reported.

Utility

The radiopharmaceuticals provided herein are useful as imaging agents for the diagnosis of cardiovascular disorders, such as thromboembolic disease or atherosclerosis, infectious disease and cancer. The radiopharmaceuticals are comprised of phosphine or arsine ligated technetium-99m labeled hydrazino or diazenido modified biologically active molecules that selectively localize at sites of disease and thus allow an image to be obtained of the loci using gamma scintigraphy. The complexes described in Examples 1–3 were evaluated for potential clinical utility as radiopharmaceuticals for the diagnosis of thromboembolic disease by performing imaging studies in a canine model of deep vein thrombosis. The blood clearance rates for the complexes were determined in the arteriovenous shunt model. Said imaging studies showed that the radiopharmaceuticals provided herein are useful in imaging thrombosis.

Canine Deep Vein Thrombosis Model: This model incorporates the triad of events (hypercoagulatible state, period of stasis, low shear environment) essential for the formation of a venous fibrin-rich actively growing thrombus. The procedure was as follows: Adult mongrel dogs of either sex (9–13 kg) were anesthetized with pentobarbital sodium (35 mg/kg, i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel which serves as an indirect measure of venous flow. A balloon embolectomy catheter was utilized to induce the 15 min period of stasis during which time a hypercoagulatible state was then induced using 5 U thrombin (American Diagnosticia, Greenwich Conn.) administered into the occluded segment. Fifteen minutes later, flow was reestablished by deflating the balloon. The radiopharmaceutical was infused during the first 5 minutes of reflow and the rate of incorporation monitored using gamma scintigraphy.

Arteriovenous Shunt Model. Adult mongrel dogs of either sex (9–13 kg) were anesthetized with pentobarbital sodium (35 mg/kg,i.v.) and ventilated with room air via an endotracheal tube (12 strokes/min, 25 ml/kg). For arterial pressure determination, the left carotid artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo,), saline filled polyethylene tubing (PE-200) and connected with a 5 cm section of silicon treated tubing (PE-240) to form an extracorporeal arterio-venous shunts (A-V). Shunt patency was monitored using a doppler flow system (model VF-1, Crystal Biotech Inc, Hopkinton, Mass.) and flow probe (2–2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 min post surgical stabilization period, an occlusive thrombus was formed by the introduction of a thrombogenic surface (4-0 braided silk thread, 5 cm in length, Ethicon Inc., Somerville, N.J.) into the shunt one shunt with the other serving as a control. Two consecutive 1hr shunt periods were employed with the test agent administered as an infusion over 5 min beginning 5 min before insertion of the thrombogenic surface. At the end of each 1 hr shunt period the silk was carefully removed and weighed and the % incorporation determined via well counting. Thrombus weight was calculated by subtracting the weight of the silk prior to placement from the total weight of the silk on removal from the shunt. Arterial blood was withdrawn prior to the first shunt and every 30 min thereafter for determination of blood clearance, whole blood collagen-induced platelet aggregation, thrombin-induced platelet degranulation (platelet ATP release), prothrombin time and platelet count. Template bleeding time was also performed at 30 min intervals.

Results

The results of the imaging studies performed on the radiopharmaceuticals of Examples 1 and 2 are shown in FIG. 2 and Tc-99m-albumin, a negative control. The top graph shows the thrombus-to-blood ratios, the bottom graph shows the thrombus-to muscle ratios obtained from the images by drawing appropriate regions of interest and comparing the number of counts in each region. The values reported are for the images obtained at 15, 60 and 120 minutes after the end of the infusion of the compounds. Even as early as 15 minutes, the three radiopharmaceuticals have higher ratios than the negative control; the differences are pronounced by 60–120 minutes.

Complexes in which the biologically active molecules, Q, are chemotactic peptides can be evaluated for potential clinical utility as radiopharmaceuticals for the diagnosis of infection by performing imaging studies in a rabbit model of focal infection.

Rabbit Focal Infection Model

Using aseptic technique, adult rabbits of either sex (2–3 kg) were anesthetized with Ketamine/xylazine (15/1.5 mg/kg, i.v.) via the marginal ear vein. Each animal was administered a 1 ml suspension of 2×10E9 of E Coli in the posterior thigh muscle. At the appropriate time point, 18–48 hrs later, each animal was anesthetized with pentobarbital sodium (35 mg/kg, i.v.). A tracheotomy was then performed and the animal ventilated with room air using a rodent respirator. For arterial pressure determination, the left carotid artery was cannulated with a saline-filled polyethylene catheter and connected to a pressure transducer. Mean arterial blood pressure was determined via damping the pulsatile pressure signal. Heart rate was monitored using a cardiotachometer triggered from a lead II electrocardiogram generated by limb leads. A jugular vein was cannulated for drug administration. All parameters were monitored continuously on a polygraph recorder.

On completion of a 15 min post surgical stabilization period, the agent was infused over 1–5 min (1–20 mCi). On line assessment of the rate of incorporation into the inflammatory site was accomplished using serial scintigrams acquired at 0–3 and 18–24 hrs posttreatment. Images were acquired for a preset time of 5 min/view. To characterize the location of the peptide, region of interest analysis was performed comparing the infected thigh to the contralateral normal muscle at the corresponding time. Arterial blood was withdrawn prior to administration and every 30 min thereafter for determination of blood clearance, hematological profile and white blood cell function. On completion of the protocol, the animal was euthanized and the biodistribution of the compound determined via gamma well counting.

We claim:

1. A radiopharmaceutical comprising a transition metal radionuclide ($M_t$), a transition metal chelator ($C_{h'}$), a biologically active group (Q) connected to said chelator, a first ancillary ligand ($A_{L1}$), a second ancillary ligand ($A_{L2}$) capable of stabilizing the radiopharmaceutical, optionally having a linking group ($L_n$) between said chelator and said biologically active group, wherein:

$C_{h'}$ is a radionuclide metal chelator coordinated to $M_t$, and is independently selected at each occurrence, from the group: $R^{40}N{=}N^+{=}$, $R^{40}R^{41}N{-}N{=}$, $R^{40}N{=}$, and $R^{40}N{=}N(H){-}$;

$R^{40}$ is independently selected at each occurrence from the group: a bond to $L_n$, $C_1$–$C_{10}$ alkyl substituted with 0–3 $R^{52}$, aryl substituted with 0–3 $R^{52}$, cycloaklyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$R^{41}$ is independently selected from the group: hydrogen, aryl substituted with 0–3 $R^{52}$, $C_1$–$C_{10}$ alkyl substituted with 0–3 $R^{52}$, and a heterocycle substituted with 0–3 $R^{52}$;

$R^{52}$ is independently selected at each occurrence from the group: a bond to $L_n$, =O, F, Cl, Br, I, —$CF_3$, —CN, —$CO_2R^{53}$, —C(=O)$R^{53}$, —C(=O)N($R^{53}$)$_2$, —CHO, —$CH_2OR^{53}$, —OC(=O)$R^{53}$, —OC(=O)O$R^{53a}$, —O$R^{53}$, —OC(=O)N($R^{53}$)$_2$, —$NR^{53}$C(=O)$R^{53}$, —$NR^{54}$C(=O)O$R^{53a}$, —$NR^{53}$C(=O)N($R^{53}$)$_2$, —$NR^{54}SO_2N(R^{53})_2$, —$NR^{54}SO_2R^{53a}$, —$SO_3H$, —$SO_2R^{53a}$, —$SR^{53}$, —S(=O)$R^{53a}$, —$SO_2N(R^{53})_2$, —N($R^{53}$)$_2$, —NHC(=NH)$NHR^{53}$, —C(=NH)$NHR^{53}$, =$NOR^{53}$, $NO_2$, —C(=O)$NHOR^{53}$, —C(=O)$NHNR^{53}R^{53}a$, —$OCH_2CO_2H$, and 2-(1-morpholino)ethoxy; and $R^{53}$, $R^{53a}$, and $R^{54}$ are each independently selected at each occurrence from the group: hydrogen, $C_1$–$C_6$ alkyl, and a bond to $L_n$.

2. A radiopharmaceutical of claim 1, wherein:

$C_{h'}$ is a radionuclide metal chelator coordinated to Mt, and is independently selected at each occurrence, from the group: $R^{40}N\!=\!N^+\!=\!$, and $R^{40}R^{41}N\!-\!N\!=\!$;

$R^{40}$ is independently selected at each occurrence from the group: heterocycle substituted with $R^{52}$;

$R^{41}$ is hydrogen; and, $R^{52}$ is a bond to $L_n$.

3. A radiopharmaceutical of claim 1 having a linking group ($L_n$) between said chelator and said biologically active group.

4. A radiopharmaceutical of claim 3, wherein: $L_n$ is a linking group of formula:

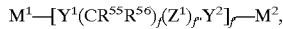

$M^1$ is $-[(CH_2)_g Z^1]_{g'}-(CR^{55}R^{56})_{g''}-$;

$M^2$ is $-(CR^{55}R^{56})_{g''}-[Z^1(CH_2)_g]_{g'}-$;

g is independently 0–10;

g' is independently 0–1;

g" is independently 0–10;

f is independently 0–10;

f' is independently 0–10;

f" is independently 0–1;

$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$;

$Z^1$ is independently selected at each occurrence from a $C_6$–$C_{14}$ saturated, partially saturated, or aromatic carbocyclic ring system, substituted with 0–4 $R^{57}$, and a heterocyclic ring system, substituted with 0–4 $R^{57}$;

$R^{55}$ and $R^{56}$ are independently selected at each occurrence from: hydrogen; $C_1$–$C_{10}$ alkyl substituted with 0–5 $R^{57}$; and alkaryl wherein the aryl is substituted with 0–5 $R^{57}$;

$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)$NR^{58}$—, C=N, $SR^{58}$, $SOR^{58}$, $SO_2R^{58}$, NHC(=O)$R^{58}$, NHC(=O)$NHR^{58}$, NHC(=S)$NHR^{58}$; or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C(=O)$, and $(NH)_2C=S$; and, $R^{58}$ is independently selected at each occurrence from the group: hydrogen, $C_1$–$C_6$ alkyl, benzyl, and phenyl;

x and y are independently 1 or 2; and, z is independently 1–4.

5. A radiopharmaceutical of claim 4 wherein: $L_n$ is a linking group of formula:

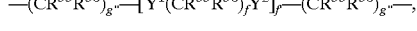

g" is 0–5;

f is 0–5;

f' is 1–5;

$Y^1$ and $Y^2$, at each occurrence, are independently selected from: O, $NR^{56}$, C=O, C(=O)O, OC(=O)O, C(=O)NH—, C=$NR^{56}$, S, NHC(=O), $(NH)_2C(=O)$, and $(NH)_2C=S$;

$R^{55}$ and $R^{56}$ are hydrogen;

x and y are 1; and, z is 1.

6. A radiopharmaceutical of claim 1, wherein $A_{L1}$ is selected from the group: dioxygen ligand, functionalized aminocarboxylate, and halide.

7. A radiopharmaceutical of claim 6, wherein $A_{L1}$ is tricine.

8. A radiopharmaceutical of claim 1, wherein $A_{L2}$ is selected from the group:

$A^9$ and $A^{10}$—W—$A^{11}$;

$A^9$ is independently selected at each occurrence from the group: $PR^{61}R^{62}R^{63}$ and $AsR^{61}R^{62}R^{63}$;

$A^{10}$ and $A^{11}$ are independently selected at each occurrence from the group: $PR^{61}R^{62}$ and $AsR^{61}R^{62}$;

W is a spacer group selected from the group: $C_1$–$C_{10}$ alkyl substituted with 0–3 $R^{70}$, aryl substituted with 0–3 $R^{70}$, cycloalkyl substituted with 0–3 $R^{70}$, heterocycle substituted with 0–3 $R^{70}$, heterocycloalkyl substituted with 0–3 $R^{70}$, aralkyl substituted with 0–3 $R^{70}$, and alkaryl substituted with 0–3 $R^{70}$;

$R^{61}$, $R^{62}$, and $R^{63}$ are independently selected at each occurrence from the group: $C_1$–$C_{10}$ alkyl substituted with 0–3 $R^{70}$, aryl substituted with 0–3 $R^{70}$, cycloalkyl substituted with 0–3 $R^{70}$, heterocycle substituted with 0–3 $R^{70}$, aralkyl substituted with 0–3 $R^{70}$, alkaryl substituted with 0–3 $R^{70}$, and arylalkaryl substituted with 0–3 $R^{70}$;

$R^{70}$ is independently selected at each occurrence from the group: F, Cl, Br, I, —$CF_3$, —CN, —$CO_2R^{71}$, —C(=O)$R^{71}$, —C(=O)N($R^{71}$)$_2$, —$CH_2OR^{71}$, —OC(=O)$R^{71}$, —OC(=O)O$R^{71a}$, —O$R^{71}$, —OC(=O)N($R^{71}$)$_2$, —$NR^{71}$C(=O)$R^{71}$, —$NR^{71}$C(=O)O$R^{71}$, —$NR^{71}$C(=O)N($R^{71}$)$_2$, $SO_3^-$, —$NR^{71}SO_2N(R^{71})_2$, —$NR^{71}SO_2R^{71a}$, —$SO_3H$, —$SO_2R^{71}$, —S(=O)$R^{71}$, —$SO_2N(R^{71})_2$, —N($R^{71}$)$_2$, —N($R^{71}$)$_3^+$, —NHC(=NH)$NHR^{71}$, —C(=NH)$NHR^{71}$, =NO$R^{71}$, $NO_2$, —C(=O)$NHOR^{71}$, —C(=O)$NHNR^{71}R^{71a}$, and —$OCH_2CO_2H$; and, $R^{71}$ and $R^{71a}$ are independently selected at each occurrence from the group: hydrogen and $C_1$–$C_6$ alkyl.

9. A radiopharmaceutical of claim 8, wherein $A_{L2}$ is $PR^{61}R^{62}R^{63}$;

$R^{61}$, $R^{62}$, and $R^{63}$ are independently selected at each occurrence from the group: $C_1$–$C_3$ alkyl substituted with 0–3 $R^{70}$, aryl substituted with 0–3 $R^{70}$; and, $R^{70}$ is independently selected at each occurrence from the group: —$CO_2H$, —OH, —$SO_3H$, and —$SO_3$—.

10. A radiopharmaceutical of claim 1, wherein $M_t$ is selected from the group: $^{99m}$Tc, $^{186}$Re and $^{188}$Re.

11. A radiopharmaceutical of claim 10, wherein $M_t$ is $^{99m}$Tc.

12. A radiopharmaceutical of claim 1, wherein Q is:

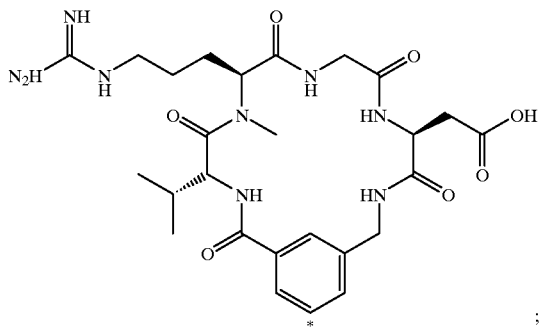

and
$L_n$ is attached at the carbon atom designated with an *.

13. A radiopharmaceutical of claim 4, wherein Q is:

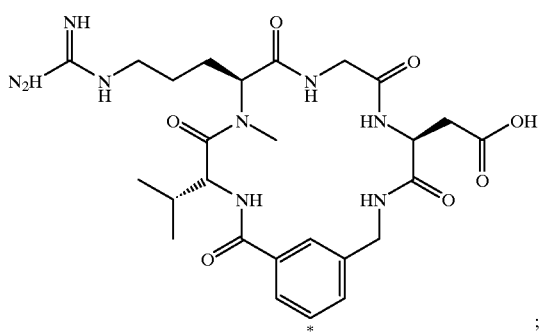

and
$L_n$ is attached at the carbon atom designated with an *.

14. A radiopharmaceutical of claim 6, wherein Q is:

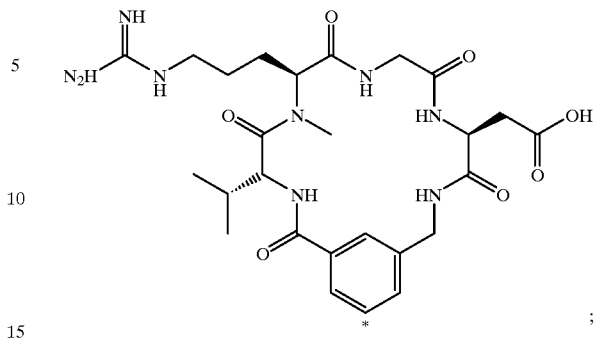

and
$L_n$ is attached at the carbon atom designated with an *.

15. A radiopharmaceutical of claim 8, wherein Q is:

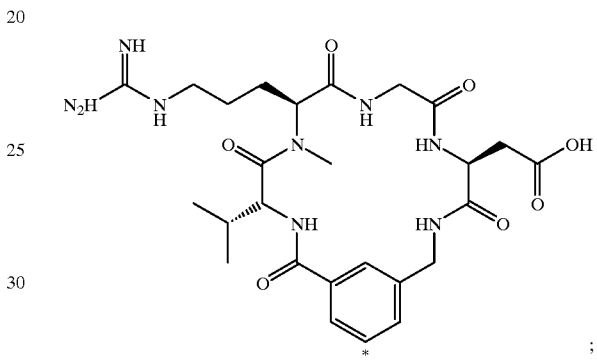

and
$L_n$ is attached at the carbon atom designated with an *.

* * * * *